US005697132A

United States Patent [19]

DeCarbo, Sr. et al.

[11] Patent Number: 5,697,132
[45] Date of Patent: Dec. 16, 1997

[54] SYSTEM AND METHOD FOR AUTOMATED MIXING AND DELIVERY OF EMBALMING FLUID TO A CADAVER

[75] Inventors: Roger M. DeCarbo, Sr., New Castle; John R. Paulik, Wexford, both of Pa.

[73] Assignee: Morganthal LLC, New Castle, Pa.

[21] Appl. No.: 664,590

[22] Filed: Jun. 17, 1996

[51] Int. Cl.[6] ................................................ A01N 1/00
[52] U.S. Cl. ........................... 27/22.1; 27/23.1; 222/145.5
[58] Field of Search ................................. 27/21.1, 22.1, 27/23.1, 24.1, 24.2; 222/64, 51, 144.5, 145.6, 134

[56] References Cited

U.S. PATENT DOCUMENTS

| | | | |
|---|---|---|---|
| 2,296,539 | 9/1942 | Salle | 27/22.1 |
| 3,528,146 | 9/1970 | Markarian | |
| 4,392,508 | 7/1983 | Switall | |
| 4,691,850 | 9/1987 | Kirschmann | |
| 4,901,410 | 2/1990 | Fischer | |
| 4,980,956 | 1/1991 | Fischer | |
| 4,982,481 | 1/1991 | Deutscher | 27/21.1 |
| 5,020,917 | 6/1991 | Homan | |
| 5,234,268 | 8/1993 | Homan | |
| 5,507,412 | 4/1996 | Ebert | |
| 5,584,327 | 12/1996 | Thomas et al. | 222/145.5 |

Primary Examiner—Kien T. Nguyen
Attorney, Agent, or Firm—Jones, Day, Reavis & Pogue

[57] ABSTRACT

An automated system and method are provided for continuous-flow delivery of a desired mixture of embalming chemicals and water to a cadaver. The invention may be used with any liquid that has substantially the same viscosity as water. At least two embalming chemical concentrates of a plurality of different embalming chemicals are selectively delivered to a mixing manifold via at least two primary fluid conduits, for continuous mixing with a continuous flow of water through the manifold. The resulting embalming chemical and water mixture is delivered to the cadaver. Proportional quantities of chemicals and water flowing through the mixing manifold are metered by proportional flow valves for accurate mixing and dilution of the chemicals. A microprocessor controller is programmed to control the flow and the rate of flow of chemicals and water through the mixing manifold and the fluid conduits. The invention further provides for automated aspiration of and delivery of cavity fluids to the cadaver.

24 Claims, 6 Drawing Sheets

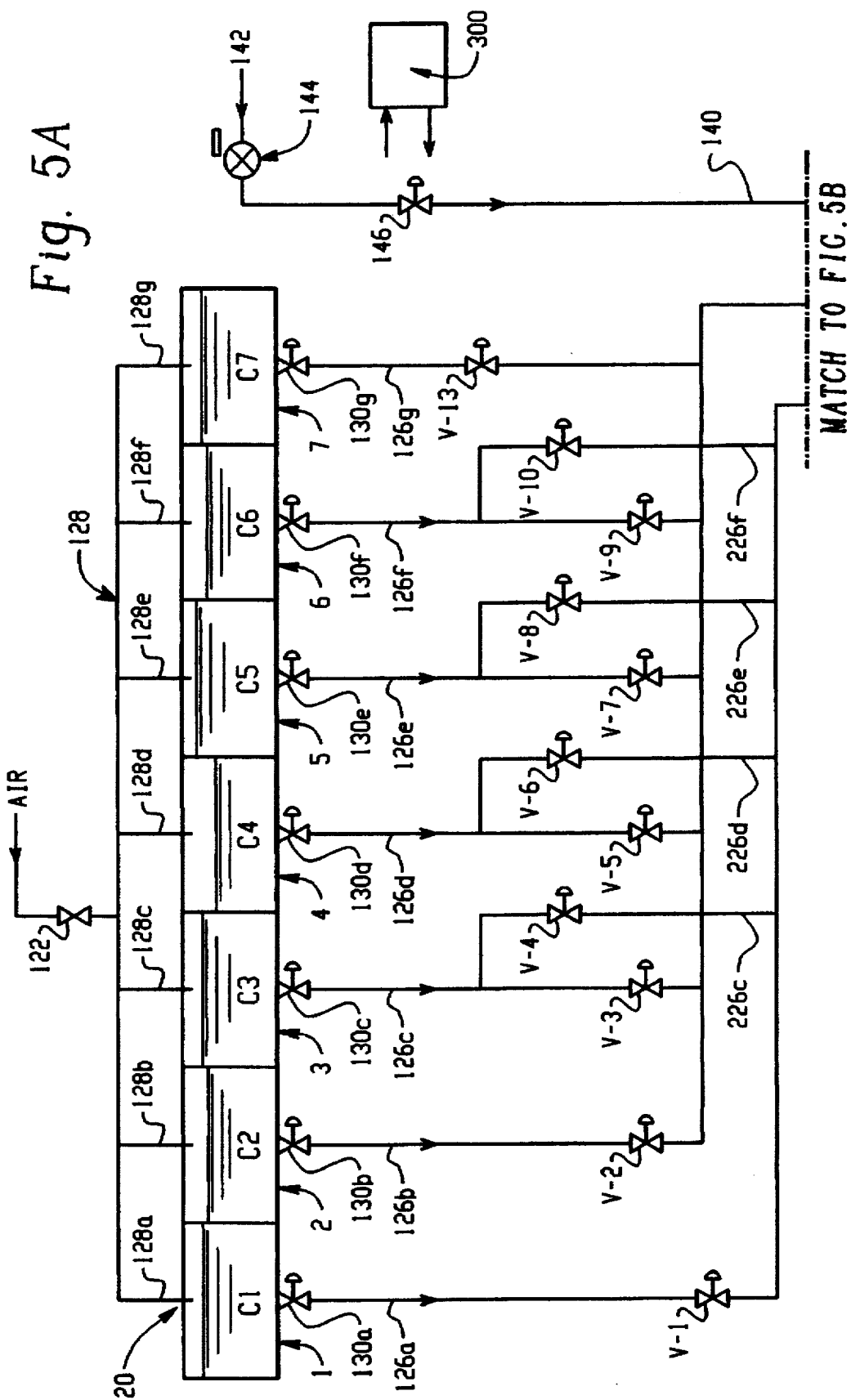

SYSTEM AND METHOD FOR AUTOMATED MIXING AND DELIVERY OF EMBALMING FLUID TO A CADAVER

BACKGROUND OF THE INVENTION

The process of embalming a cadaver for purposes of disinfection, restoration and preservation may involve the use of many different embalming chemicals, including mixtures containing formaldehyde, glutaraldehyde, alcohols and/or phenols, in varied combinations. Typically, individual embalming chemicals are supplied in 16-ounce bottles. An appropriate combination of the embalming chemicals is selected by the operator and manually added to a premeasured amount of water in a reservoir in an embalming machine. The resulting diluted embalming fluid mixture is then pumped from the reservoir, through tubing that terminates in a cannula or other device, into an artery of the cadaver.

A major concern with known embalming procedures is that the embalmer and other personnel may be exposed to a considerable accumulation of hazardous and potentially carcinogenic formaldehyde liquids and vapors. Exposure frequently occurs, for example, during the pouring of chemicals into the embalming machine reservoir, the disposal of unused embalming fluid from the reservoir, the disposal of used embalming chemical bottles and accidental spillages. Because current embalming machines do not provide the ability to easily change the fluid delivery flow rate or pressure, unexpected blockages to the delivery may cause an abrupt fluid spray exposure to the embalmer. Embalming machines that employ refillable bulk chemical containers and deliver set quantities of chemicals to the reservoir are known. However, these machines require the operator to refill the chemical containers from the small bottles and do not address the problem of exposure to harmful liquids or vapors.

A further problem with current embalming methods is the necessity of employing differing mixtures of embalming fluids for each procedure. Thus, the embalming reservoir must be emptied, cleaned and refilled between procedures. Frequently, during a single procedure, a special chemical additive or even an entirely different embalming fluid mixture is found to be necessary for proper embalming. Again the embalming reservoir must be emptied and refilled with the new mixture. Further, the quantity of embalming fluid required for a single procedure is unpredictable and fluid remaining in the reservoir at the end of the procedure is wasted and requires disposal. Purchase of embalming chemicals packaged in small 16-ounce bottles is costly compared to bulk purchasing and storage of the small bottles is an inefficient use of floor and storage space. Thus, current systems for embalming are inefficient, wasteful of time and materials, and potentially harmful to embalming personnel.

A need exists, therefore, for an automated embalming system that efficiently provides differing chemical mixtures of embalming fluids to a cadaver, as needed, without exposing personnel to harmful liquids and vapors and without waste of valuable embalming fluids.

SUMMARY OF THE INVENTION

The present invention is a system and method for automated, continuous-flow delivery of a desired mixture of embalming chemicals and water to a cadaver. The invention eliminates the necessity for manual mixing of the embalming chemicals and water in a mixing reservoir, and employs bulk embalming chemicals in an enclosed, sealable environment. Thus, the invention eliminates the problems of personnel exposure to hazardous liquids and vapors, and waste of valuable embalming fluids, storage space and personnel time.

The apparatus comprises a mobile, self-contained, enclosed and sealable unit, such as a cabinet, that holds a plurality of bulk containers of differing embalming chemical concentrates in fluid communication via fluid supply conduits with a mixing manifold. A microprocessor, preferably a programmable logic controller, is programmable by the user to automatically and continuously deliver a desired chemical or mixture of chemicals into a flow of water in the mixing manifold according to a selected recipe. A plurality of programs specifying different embalming chemical mixtures, delivery pressures and flow rates may be pre-programmed into the controller. The programs may also be manually altered by the operator and the altered programs stored into the controller memory.

Chemicals from the plurality of containers are selectively drawn, by a pump having a variable speed pump motor, through individual fluid conduits into at least two primary fluid conduits that terminate at inlet ports of the mixing manifold. Water from a standard water source is allowed to flow through the mixing manifold. Proportional quantities of chemicals and water flowing through the mixing manifold are metered by proportional flow valves, so that not only is an accurate mixture of the embalming chemicals obtained, but an accurate dilution of the fluid mixture with water is also obtained. From the mixing manifold, the desired fluid mixture is delivered by tubing or other conduit into an artery of the cadaver.

The delivery pressure and flow rate are variable and pre-programmable, but the delivery pressure may be manually altered or adjusted during a procedure by means of a user control on a user control panel. The operator may also use the user control to control other parameters, such as the start and stop of the pump motor, the changing of programmed fluid mixtures, and the selection of the embalming fluid delivery or the aspiration function. A feature of the invention is that the user control may be a remote control device and placed within easy reach of the embalmer for controlling the delivery parameters, including a change in the embalming fluid mixture, during an embalming procedure.

Another feature of the invention is designed to minimize the likelihood that the embalmer is exposed to an unexpected fluid spray when an unexpected blockage to the fluid delivery is encountered. By the invention, a pressure switch in the fluid output conduit senses back-pressure during delivery of the fluid mixture to the cadaver. If the back-pressure in the conduit exceeds a predetermined delivery pressure value, the pressure switch closes and sends a signal to the controller to turn off the pump motor.

By the invention, the controller is programmed to provide a fluid delivery pressure that does not exceed a predetermined maximum value and to activate a shut-off valve to turn off the pump motor if that value is exceeded. Thus, for example, small blockages in an artery may be dislodged by pressures up to the maximum value.

An aspiration and waste discharge function are provided in the system of the invention. The system also provides a self-flushing capability for periodic flushing of the mixing manifold, the pump, the aspiration and discharge conduits, and the like.

The system and method of the invention for continuous-flow mixing of liquids and water may be used with any liquid that has substantially the same viscosity as water. According to the invention, a plurality of containers, each containing a fluid that is preferably an embalming chemical, are provided. A first fluid supply conduit fluidly connects a first container with a first inlet port of a mixing manifold that comprises a hollow chamber having a plurality of inlet ports and an outlet port. A second fluid supply conduit fluidly connects a second container with a second inlet port of the mixing manifold. A plurality of other fluid supply conduits, each of which fluidly connects another container of the plurality of containers, are fluidly connected with the first and the second fluid supply conduits. By the selective opening and closing of a plurality of multi-directional valves, each of which is fluidly connected to at least one fluid supply conduit, a selected chemical is drawn into the first conduit and another selected chemical is drawn into the second conduit and both chemicals flow to the mixing manifold.

A first proportional flow valve, in fluid communication with the first conduit, controls the rate of flow from the first conduit into the first inlet port of the mixing manifold. A second proportional flow valve, in fluid communication with the second conduit, controls the rate of flow from the second conduit into the second inlet port of the mixing manifold. A third proportional flow valve similarly controls the rate of flow of water from a water supply conduit into a third inlet port of the mixing manifold. Thus, by selectively controlling each multi-directional valve to allow the flow of a selected fluid from the plurality of containers into the first or second conduits, a mixture of fluids may enter the mixing manifold for mixing with water.

A controller is preferably in electronic communication with the proportional flow valves, the multi-directional valves and the pump, and is programmed to control the flow and the rate of flow of fluid and water through the mixing manifold and the fluid conduits.

DETAILED DESCRIPTION OF THE INVENTION

Reference will now be made in detail to the present preferred embodiment of the invention, an example of which is illustrated in the accompanying drawings.

Figure 1:
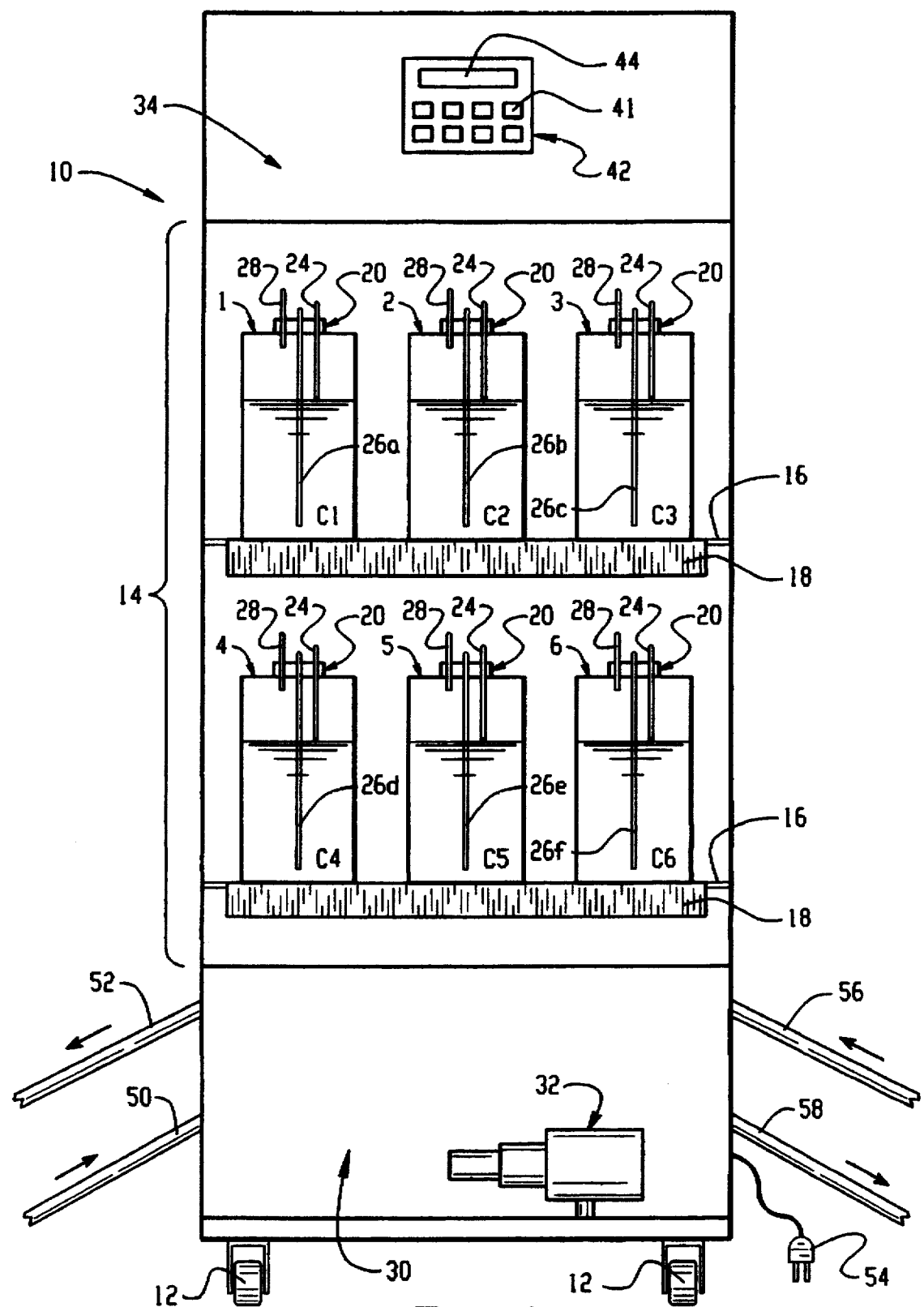
FIG. 1 is a schematic cut-away illustration of the self-contained unit containing the apparatus of the invention.
Figure 2:
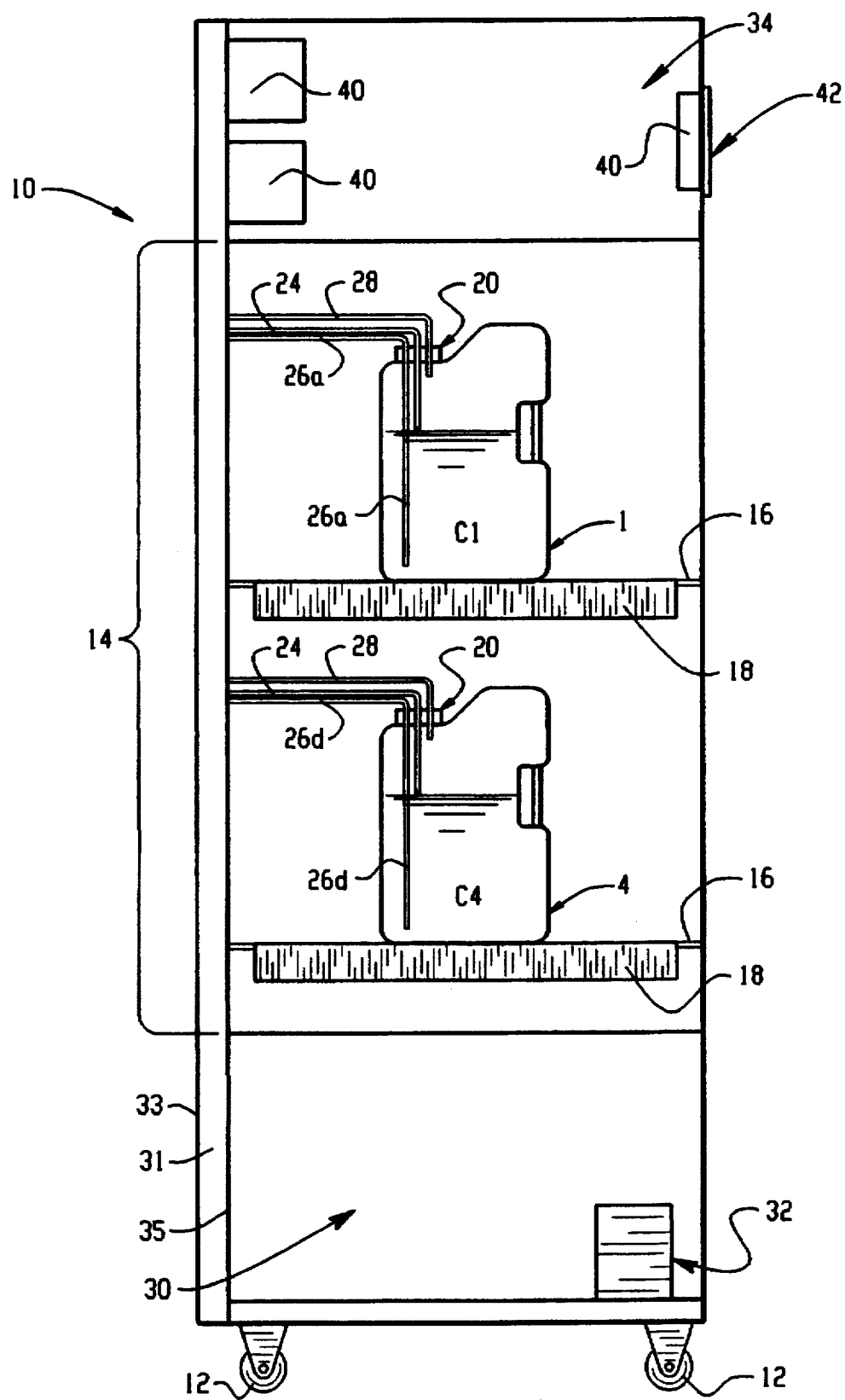
FIG. 2 is a schematic cut-away side view of the unit containing the apparatus of the invention.

The embalming apparatus of the present invention, illustrated in FIGS. 1 and 2, is housed in a sealable cabinet preferably having a plurality of lockable wheels 12 to facilitate easy movement, relocation and securing of the cabinet position. The embalming apparatus includes a suction conduit 50 and a fluid output conduit 52 that terminate in a needle, cannula, trocar or like device (not shown) for respectively aspirating material from or delivering embalming fluid to the cadaver. The conduits 50, 52 extend exteriorly from the cabinet 10 to allow both aspiration and embalming functions to be performed utilizing this single apparatus. Other external connections to the cabinet 10 include wires terminated in a plug 54 for receiving AC electric power from a standard wall outlet, a water supply conduit 56 for connecting with a standard or distilled water source, a water/suction discharge conduit 58 leading to a drain (not shown).

A plurality of closed embalming chemical containers, illustrated as six containers 1, 2, 3, 4, 5, 6, containing embalming chemicals or liquid chemical concentrates C1, C2, C3, C4, C5, C6 are positioned within a sealable section 14 of the cabinet 10. Preferably, a sealable door (not shown) is provided to facilitate access to at least the fluid container section 14 of the cabinet 10. As described below, two or more of the containers may contain identical, frequently-used primary embalming chemical concentrates. The containers 1–6 may be of any size that will accommodate individual embalming chemicals C1–C6 in bulk and conveniently fit into a given cabinet 10. Preferably, the containers are capable of holding at least two gallons, and more preferably, about three gallons of embalming chemicals. For large operations it may be desirable to supply larger bulk fluid quantities. Preferably, the containers are disposable and the bulk embalming chemicals inexpensive, to discourage refilling by embalming personnel from the smaller, more expensive bottles, as described above.

The containers 1–6 rest on one or more shelves 16 each of which includes a leak collection tray 18 that preferably has a capacity in excess of the maximum volume of the stored embalming chemicals C1–C6 on the shelf 16. Each of the containers 1–6 is sealingly fitted with a sealed pumping adapter 20 to enable the embalming chemicals C1–C6 to be drawn from the closed containers 1–6 through fluid supply conduits 26a, 26b, 26c, 26d, 26e, 26f. Each pumping adapter 20 also includes an air line 28, including a one-way valve, illustrated further in FIG. 5, to allow air to enter the closed containers 1–6 and prevent leakage of chemical gases to the atmosphere. Each pumping adapter 20 may include a low-level sensor 24 for each fluid C1–C6 in the containers 1–6. Alternatively, the fluid levels may be monitored indirectly by a microprocessor control device (described below), by monitoring the volume of fluid passing through a proportional flow valve (described below) and subtracting that amount from the known starting volume in the container.

Figure 3:
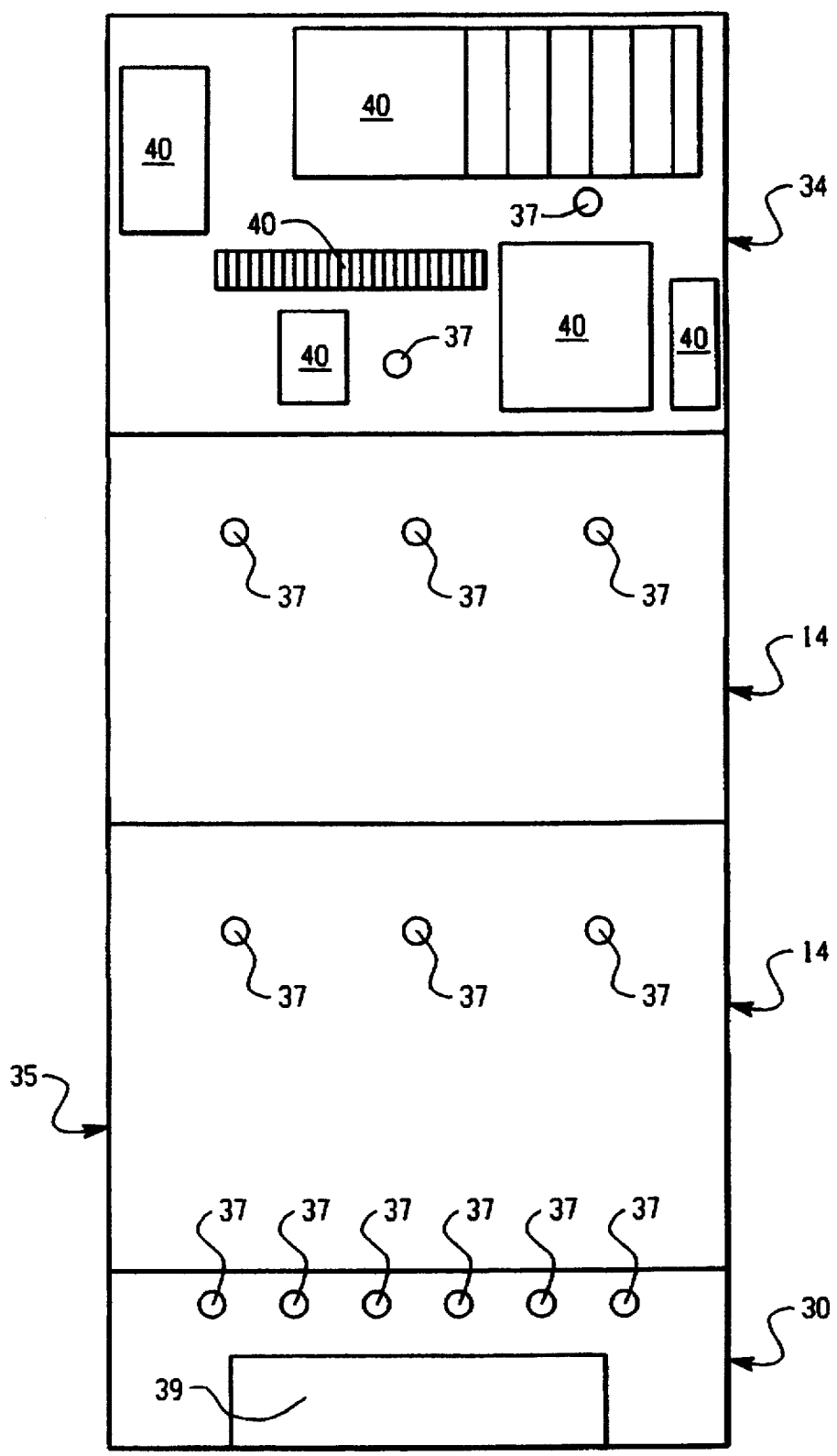
FIG. 3 is a schematic front view of the rear sub-panel of the unit containing the apparatus of the invention.

A section 30 of the cabinet 10 is sealingly isolated from section 14 and contains a pump 32 for drawing the embalming chemicals C1–C6 from the containers 1–6 and also contains various components 39, such as conduits, electrical lines, valves and mixing manifold, as described below. As illustrated in FIGS. 2 and 3, a space 31 is provided between a rear cabinet panel 33 and a sub-panel 35, having sealable openings 37, to accommodate passage of, for example, conduits, hoses, and electrical wires for connecting the various components of the apparatus.

Another section 34 of the cabinet 10, illustrated in FIGS. 1, 2 and 3, is sealed from the other cabinet sections 14, 30 and contains a control device 40, preferably a microprocessor, and more preferably a programmable logic controller. The control device 40 is in electronic communication with and controllably operates various valves, the pump and other mechanical parts of the embalming apparatus, as described below and illustrated in FIG. 5. User controls 41 for programming the control device 40 are located on a user control panel 42 that is exterior to the sealed cabinet section 34 for accessibility to the operator. Preferably, the user controls 41 are located on a touch screen panel; however, any suitable type of user controls such as switches or buttons, may be employed. The user controls 41 include, but are not limited to, a pump on-off switch for energizing the AC system, an embalm-aspirate switch for choosing one or the other of the functions to be performed by the device, and means for electronically pre-programming system parameters, such as fluid flow rate, delivery pressure and embalming fluid mixture selection. Preferably, the user control panel 42 includes a display unit 44 for displaying selected program parameters, instructions, error messages, and warnings, including low liquid level warnings. The control device 40 includes an audible alarm system including, but not limited to, an alarm for indicating that a manually operated water supply valve is closed. Such control systems are known and are not a part of the present invention.

Figure 4:
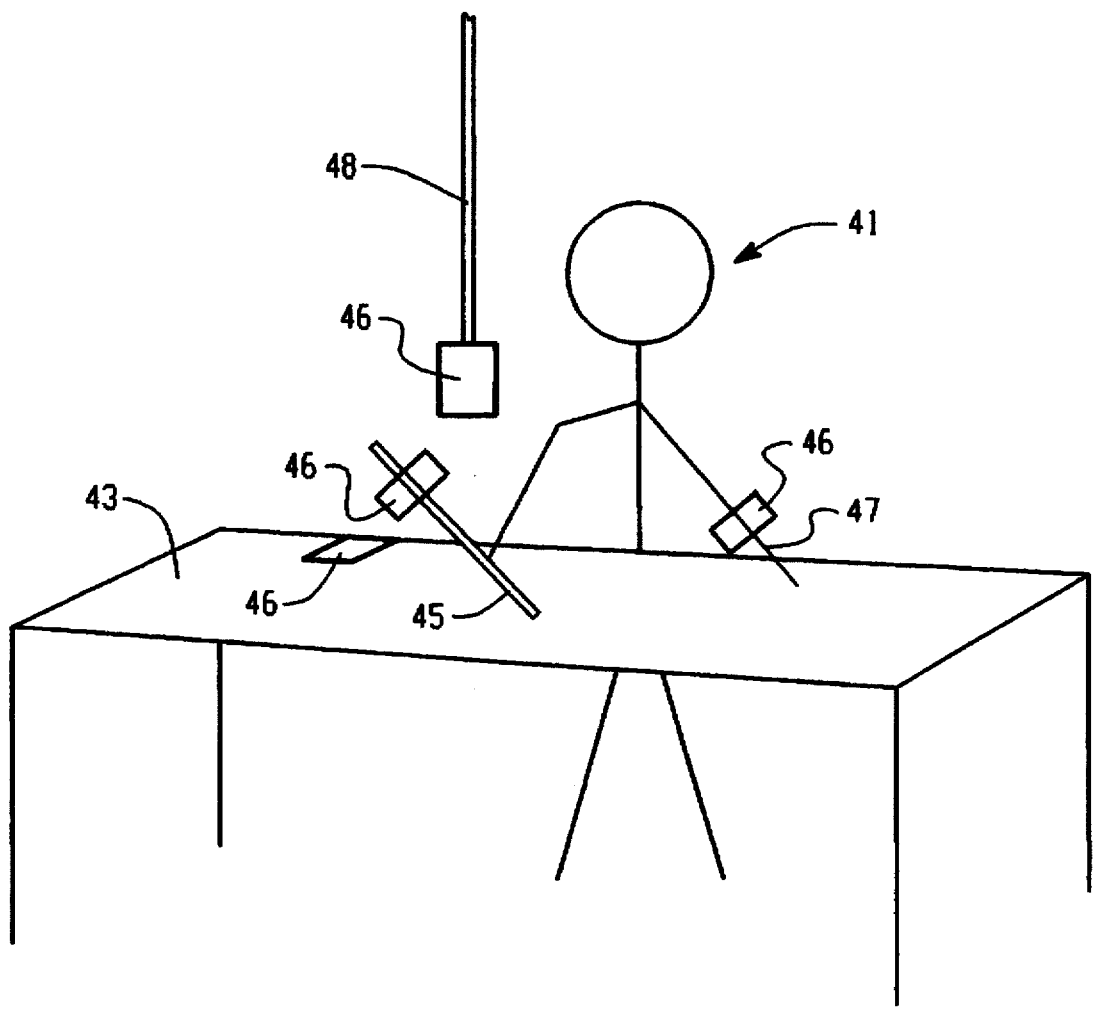
FIG. 4 is a stick-figure illustration of possible locations near an embalmer for the remote-control programming device of the invention.

As illustrated in FIG. 4, one or more auxiliary manually operated user control devices 46, which are preferably remote control devices, are provided within convenient and easy reach of the embalmer 41 during the embalming procedure. For example, the auxiliary user control device 46 may be provided on a free-hanging pendant 48 electrically connected to or in electronic communication with the control device 40 within the cabinet 10. Alternatively, the auxiliary user control device 46 may be removably attachable to a surface, such as the embalming table 43, an embalming, aspiration or other tool adapter 45, the embalmer's wrist 47, or the like. The auxiliary user control device 46 may or may not include an auxiliary display unit (not shown). The auxiliary user control device 46 is in electronic communication with the control device 40 by any suitable means including, but not limited to, electric wiring, radio frequency transmission and infra-red transmission. The auxiliary control device 46 preferably includes, but is not limited to, manual user controls for operating the pump 32, selecting the aspiration or embalming fluid delivery function, and altering the fluid mixture selection, flow rate and pressure.

Figure 5B:
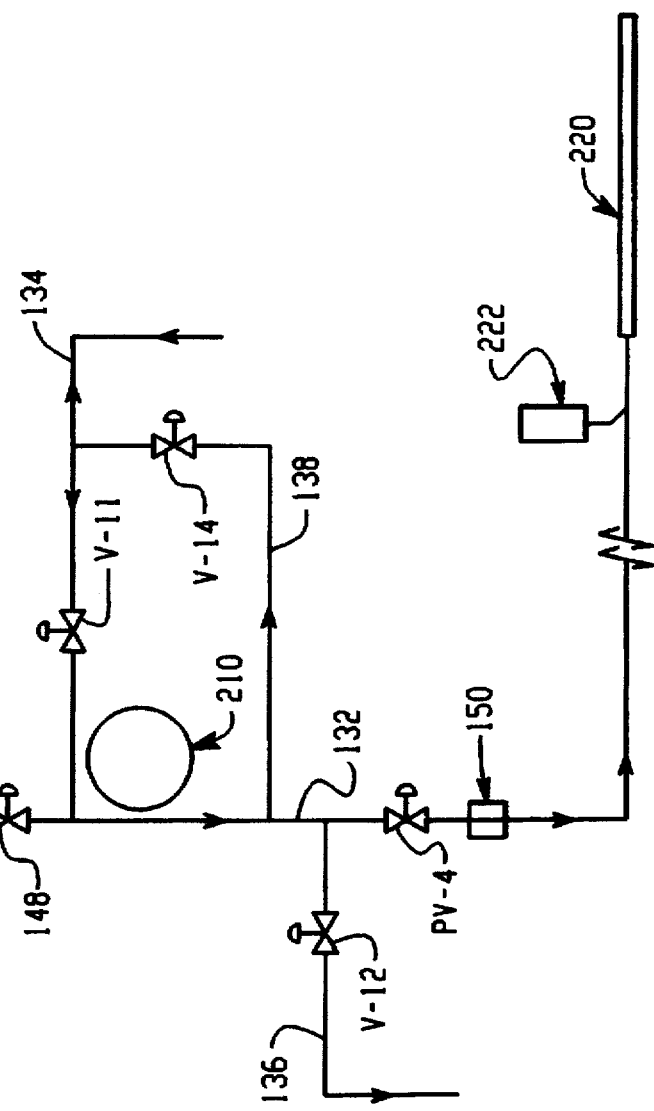
FIG. 5 is a schematic diagram of the apparatus and system of the invention.

A preferred embodiment of the embalming system of the invention is illustrated schematically in FIG. 5. As shown, seven individual embalming chemicals or liquid chemical concentrates C1, C2, C3, C4, C5, C6, C7 are contained in closed containers 1, 2, 3, 4, 5, 6, 7. Although seven embalming chemicals are illustrated, a plurality of embalming chemicals may be used in the invention. Each of the containers 1–7 is sealingly fitted with a sealed pumping adapter 20, as illustrated in FIG. 2, to enable the embalming chemicals C1–C7 to be drawn from the closed containers 1–7 through fluid supply conduits 126a, 126b, 126c, 126d, 126e, 126f, 126g to a mixing manifold 200. The pumping adapters 20 also include an air line 128 fluidly connected to each of air lines 128a, 128b, 128c, 128d, 128e, 128f, 128g that are sealably inserted in each of the containers 1–7, respectively, for providing a vacuum break to each of the closed containers as fluid is removed. One-way valve 122 in the air line 128 allows air to enter the closed containers 1–7 and prevents leakage of chemical gases to the atmosphere. Preferably, the pumping adapters 20 include low liquid level sensors, as illustrated in FIG. 1.

Each of the fluid supply conduits 126a–126g has a check valve 130a, 130b, 130c, 130d, 130e, 130f, 130g, respectively, to prevent reflux of liquid or vapors into the closed containers 1–7. In the illustrated embodiment, a fluid supply conduit 126a connects the container 1 to the mixing manifold 200 to allow the embalming chemical C1 to flow from the container 1 into the mixing manifold 200 via an inlet port 202. A two-way valve V-1, having an open and closed position, allows the flow of fluid through conduit 126a. Similarly, conduit 126b connects the container 2 to the mixing manifold 200 to allow the embalming chemical C2 to flow from the container 2 into the mixing manifold 200 via an inlet port 204. Two-way valve V-2 allows the flow of fluid through the conduit 126b. A proportional flow valve PV-1 governs the rate of flow of fluid, at a given pressure, through the conduit 126a into the mixing manifold 200. A proportional flow valve PV-2 governs the rate of flow, at a given pressure, of fluid through the conduit 126b into the mixing manifold 200. A water supply conduit 140 is connected to a standard water source 142 that has a manual water supply valve 144. A proportional flow valve PV-3 governs the rate of flow of water at a given pressure through the conduit 140 and into the mixing manifold 200 via an inlet port 206. A check valve 146 in the conduit 140 prevents reflux of fluids to the water source 142.

Each of the fluid supply conduits 126c, 126d, 126e, 126f and 126g allows the embalming chemicals C3, C4, C5, C6 and C7, respectively, to flow from the containers 3, 4, 5, 6 and 7, respectively, into the fluid supply conduit 126b, and from thence to the mixing manifold 200. Two-way valves V-3, V-5, V-7, V-9 and V-13, each having an open and closed position, control the flow of fluids through conduits 126c, 126d, 126e, 126f and 126g, respectively, to the conduit 126b. Each of the conduits 126c, 126d, 126e and 126f has an alternative branch conduit 226c, 226d, 226e and 226f, respectively, for directing fluid flow from the containers 3, 4, 5 and 6 into the conduit 126a. Two-way valves, V-4, V-6, V-8 and V-10, each having an open and closed position, control the flow of fluids through the branch conduits 226c, 226d, 226e and 226f, respectively, to conduit 126a. A selected chemical flows through conduit 126a and a selected chemical flows through conduit 126b and the two chemicals are mixed together in the mixing manifold 200. Thus, a mixture of any two of the chemicals C1–C6 is achieved by selectively flowing the desired chemical into conduit 126a or 126b. Further, it is contemplated that a plurality of fluid conduits, similar to 126a and 126b, may be fluidly connected to containers 1–6 by means of a plurality of alternative fluid conduits and to the mixing manifold, such that mixing of more than two chemicals may be achieved.

The mixture of chemicals from fluid conduits 126a and 126b is then mixed with water in the mixing manifold. Chemical concentrate C7, which may be a specialty chemical such as a cavity fluid used to embalm organs, is preferably delivered through fluid conduit 126b and the mixing manifold, directly to the cadaver, without any mixing with the other chemicals C1–C6 or with water in the manifold.

It may be desirable to reserve containers 1 and 2 for containing identical frequently-used primary embalming concentrates. Thus, when the controller display indicates a low liquid level warning in one container or the controller senses a low liquid-level condition, the program governing the immediate procedure may be manually or automatically altered to allow the controller to draw the concentrate from the second container.

The closed position of each of the two-way valves V-1 through V-10 and V-13 is preferably achieved by spring closure. Although the illustrated embodiment of the invention employs two-way valves to control the flow of fluids through the fluid supply conduits 126a–126g and 226c–226f, it is contemplated that one or more multi-directional valves may alternatively be used to control fluid flow through a plurality of fluid supply conduits.

In the embodiment illustrated in FIG. 5, the mixing manifold 200 comprises a hollow chamber for receiving an embalming chemical or chemical mixture from fluid supply conduits 126a and/or 126b and water from the water supply conduit 140 through inlet ports 202, 204 and 206, respectively. The volume of the mixing manifold 200 required for efficient mixing of the fluids and water depends upon the fluid flow rate and the pressure in the mixing manifold. Preferably, the mixing manifold 200 has a volume of at least about eight ounces. The mixing manifold 200 has at least one fluid outlet port 208. A fluid output conduit 132 is connected to the outlet port 208 for receiving the fluid output from the mixing manifold 200. For purposes of delivering embalming fluid to a cadaver, the fluid output conduit 132 may terminate in a needle, cannula, or other such intra-vessel adaptor 220. If a very small amount of a specialty chemical is required during a procedure, this chemical may be delivered as a "piggy-back" 222 with the embalming fluid mixture in fluid output conduit 132, similar to the delivery system used for intravenous delivery of small amounts of specialized drugs.

The embalming chemicals delivered to the mixing manifold 200 via the fluid supply conduits 126a and/or 126b are mixed with pressurized water from water supply conduit 140 by cyclonic action and the embalming chemical/water mixture continuously flows through outlet port 208 and fluid output conduit 132 when a pump 210 is operated, as described below. Because the chemicals used for embalming are water based, and have viscosities virtually identical with water, this cyclonic action results in thorough mixing of the chemicals with water. It is contemplated, however, that any type of mixing unit or manifold suitable for mixing chemicals with water may be used in the invention.

A pump 210, having a variable speed motor, is in fluid communication with fluid output conduit 132. A preferred type of pump is a gear pump; however, any suitable pump with a variable speed motor may be used in the invention. Preferably, the pump 210 is capable of attaining a predetermined pressure between 0 pounds per square inch (psi) and about 60 psi to draw fluids from containers 1-7 through open fluid supply conduits 126a-126g and into the mixing manifold 200 via fluid supply conduits 126a and/or 126b. Water is delivered to the mixing manifold 200 via water supply conduit 140 at a greater pressure than that supplied by the pressure of the pump 210. A check valve 148 located between the mixing manifold 200 and the pump 210 prevents reflux of fluids into the mixing manifold 200. A proportional flow valve PV-4 governs the flow rate, at a given pressure, of the diluted embalming chemical mixture through the fluid output conduit 132.

A pressure switch 150 senses back-pressure in fluid output conduit 132 during delivery of the fluid mixture to a cadaver. If the back-pressure in the conduit exceeds a predetermined delivery pressure value, the pressure switch 150 closes and sends a signal to the controller to turn off the pump motor. This situation may occur if there is an unexpected blockage to fluid delivery. As an example, the fluid is being delivered at a pump delivery pressure of 40 psi and this degree of pressure is capable of dislodging small, but not large, blockages. If a large blockage is encountered, the back pressure rises to 50 psi, the pressure switch 150 closes and the controller turns off the pump motor. By this mechanism, the likelihood of the embalmer being exposed to an unexpected fluid spray is minimized.

For supplying the aspiration function of the invention, a suction conduit 134 from the cadaver is fluidly connected to fluid output conduit 132 and is positioned between the mixing manifold 200 and the pump 210. A suction discharge conduit 136 is fluidly connected to fluid output conduit 132 and is positioned between the pump 210 and the proportional flow valve PV-4. The suction discharge conduit 136 terminates at a drain (not shown). Two-way valves V-11 and V-12, each having an open and closed, preferably a spring-closed position, fluidly connected to suction conduit 134 and suction discharge conduit 136, respectively, control the flow of suctioned materials or flush solution (as described below) through the suction conduit 134, pump 210, fluid output conduit 132, and suction discharge conduit 136 to the drain.

A second fluid output conduit 138 is fluidly connected to conduit 132 and conduit 134 to allow the flow of specialized embalming chemical C7 to cadaver organs and cavities through conduit 134 after aspiration is performed. Two-way valve V-14, having an open and closed, preferably a spring-closed position, is fluidly connected to conduit 138, to control the flow of chemical C7 through conduits 138 and 134.

A microprocessor controller 300, preferably a programmable logic controller, is in electronic communication with the pump 210, the proportional flow valves PV-1, PV-2, PV-3, and PV-4, and the two-way or multi-directional valves V-1, V-2, V-3, V-4, V-5, V-6, V-7, V-8, V-9, V-10, V-11, V-12, V-13 and V-14 for controlling the flow and the rate of flow of fluid through the conduits 126a-126g, 226c-226f, 132, 134, 136, 138 and 140 and the mixing manifold 200. The controller 300 is programmed to store at least one predetermined reference value that is equivalent to a desired fluid flow rate, and the controller is further programmed to control each proportional flow valve such that the rate of flow of fluid through each of these valves is substantially equivalent to the reference value. The controller is also programmed to store at least one predetermined reference mixture of selected fluids and is programmed to selectively open or close the two-way or multi-directional control valves to allow flowing of the selected fluids into conduits 126a or 126b, as described above. The controller may be manually programmed by means of user controls on the user control panel on the apparatus cabinet or, alternatively, may be programmed manually by a remote control device. A plurality of programs may be stored in the controller memory. As described above, program parameters may be altered at any time and the altered program stored in controller memory.

The method of the invention comprises the steps of selectively controlling the flow of fluids, such as embalming chemicals, through the plurality of fluid supply conduits by the selective opening and closing of a plurality of multi-directional valves in electronic communication with the controller; selecting an embalming chemical from the plurality of chemical containers; continuously flowing the selected fluid through a first conduit and into the first inlet port of the mixing manifold; continuously flowing another selected fluid through a second conduit and into a second inlet port of the mixing manifold; continuously flowing water from a water supply conduit into a third inlet port of the mixing manifold; controlling the rate of flow of fluids and water into the mixing manifold; and continuously delivering a mixture of embalming chemicals and water from the outlet port of the mixing manifold to a cadaver, at a selected flow rate and pressure, through a delivery conduit fluidly connected to the outlet port.

The method further comprises the steps of programming the controller to store at least one predetermined reference value that is equivalent to a desired fluid flow rate, and further programming the controller to control each proportional flow valve such that the rate of flow of fluid through each valve is substantially equivalent to the reference value.

The method further comprises the steps of programming the controller to store at least one predetermined reference mixture of selected fluids, and further programming the controller to selectively open or close the multi-directional control valves to allow the flow of the selected fluids into the first and second conduits.

The following example illustrates a process of the invention for mixing and delivering embalming fluids to a cadaver. However, the chemical liquid mixing process may be used for any liquid with a viscosity substantially identical to that of water. When a recipe for a selected embalming fluid mixture specifies mixing one part liquid C1 from container 1 with two parts of liquid C3 from container 3 and with six parts of water, the pump is turned on. Two-way valves V-1 and V-3 are open. Two-way valves V-2 and V-4 through V-14 are left in the closed position. (Due to their spring return to the closed position, no power or signal is required). Proportional flow valves PV-1, PV-2, PV-3 and PV-4 are all open. The water supply valve is opened and pressurized water flows through water supply conduit 140 to the mixing manifold 200. Liquid C1 is drawn through fluid supply conduit 126a and into the mixing manifold 200. Liquid C3 is drawn through fluid supply conduit 126c to fluid supply conduit 126b and from thence into the mixing manifold 200. Proportional flow valve PV-1 regulates the rate flow of liquid C1 into the mixing manifold. Proportional flow valve PV-2 regulates the rate flow of liquid C3 into the mixing manifold. Proportional flow valve PV-3 regulates the rate of flow of water into the mixing manifold. Proportional flow valve PV-4 regulates the rate of flow, at a given pressure, of the embalming fluid mixture through fluid output conduit 132 for delivery to the cadaver.

In another example, an embalming fluid mixture may require one part liquid C2 in container 2, two parts liquid C5 in container 5 and four parts of water. The pump is turned on. Two-way valves V-2 and V-8 are opened. Two-way valves V-1, V-3 through V-7, and V-9 through V-12 are left in the closed position. The water supply valve is opened and pressurized water flows through water supply conduit 140 to the mixing manifold 200. Liquid C2 is drawn through fluid supply conduit 126b and into the mixing manifold 200. Liquid C5 is drawn through fluid supply conduits 126e and 226e to fluid supply conduit 126a and from thence into the mixing manifold 200. Proportional flow valves PV-1, PV-2, PV-3 and PV-4 are all opened. Proportional flow valve PV-1 regulates the rate flow of liquid C5 into the mixing manifold. Proportional flow valve PV-2 regulates the rate flow of liquid C2 into the mixing manifold. Proportional flow valve PV-3 regulates the rate of flow of water into the mixing manifold. Proportional flow valve PV-4 regulates the rate of flow, at a given pressure, of the embalming fluid mixture through fluid output conduit 132 for delivery to the cadaver.

Similarly, each of the liquids C3–C6 may be mixed with each other, simply by flowing one liquid through its appropriate conduit to fluid supply conduit 126a and another liquid through its appropriate conduit to fluid supply conduit 126b, and opening or closing the appropriate valves, as described above.

To deliver chemical C7 directly from container 7 via the mixing manifold and conduit 134 to the cadaver, two-way valves V-1 through V-12 and proportional flow valves PV-1, PV-3 and PV-4 are closed. Proportional flow valve PV-2 and two-way valves V-13 and V-14 are open. The pump is turned on.

To provide the aspirating function of the invention, two-way valves V-1 through V-10, V-13 and V-14 and proportional flow valves PV-1 through PV-4 are closed. Two-way valves V-11 and V-12 are open. The pump is turned on. The aspirated materials follow a pathway from the cadaver through conduits 134, 132 and 136 to the drain. Check valve 148 prevents aspirated material from refluxing into mixing manifold 200.

The mixing chamber, conduits 132, 134, 136 and 138, and the pump may be periodically cleaned by flushing with water, as illustrated in the following examples. During all flushing procedures, proportional flow valves PV-1 and PV-2 and two-way valves V-1 through V-10 and V-13 are closed, and water supply valve 144 and proportional flow valve PV-3 are open.

To flush the mixing chamber, proportional flow valve PV-4 and two-way valves V-11 and V-14 are closed. Two-way valve V-12 is open. The pump is turned on. Water flowing through water supply conduit 140 enters the mixing chamber and then follows a pathway through conduits 132 and 136 to the drain.

To flush conduit 134, proportional flow valve PV-4 and two-way valves V-12 and V-14 are closed. Two-way valve V-11 is open. The pump is not turned on. Water flows from the mixing manifold and follows a pathway through conduits 132 and 134, and from thence to the drain. To flush conduit 138 at the same time as conduit 134, two-way valve V-14 is opened.

To flush conduit 132 and the pump, two-way valves V-11, V-12 and V-14 are closed. Proportional flow valve PV-4 is open. The pump is turned on. Water flows from the mixing manifold and flows through the pump and conduit 132, and from thence to the drain.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

We claim:

1. A continuous flow system for delivering a mixture of embalming chemicals and water to a cadaver comprising:

a plurality of containers, wherein each container contains an embalming chemical;

a mixing manifold comprising a hollow chamber and having a plurality of inlet ports and an outlet port;

a first embalming chemical supply conduit fluidly connecting a first container of the plurality of containers with a first inlet port of the mixing manifold;

a second embalming chemical supply conduit fluidly connecting a second container of the plurality of containers with a second inlet port of the mixing manifold;

a plurality of other embalming chemical supply conduits, each of the conduits fluidly connecting another container of the plurality of containers with the first and the second fluid supply conduits;

a plurality of multi-directional valves, each valve being fluidly connected to at least one embalming chemical supply conduit, wherein each valve has an open position whereby an embalming chemical flows through the fluid supply conduit and a closed position whereby the embalming chemical cannot flow through the fluid supply conduit;

a first proportional flow valve in fluid communication with the first conduit for controlling the rate of flow of the embalming chemical from the first conduit into the first inlet port of the mixing manifold;

a second proportional flow valve in fluid communication with the second conduit for controlling the rate of flow of the embalming chemical from the second conduit into the second inlet port of the mixing manifold;

a water supply conduit fluidly connected to a water source and to a third inlet port of the mixing manifold;

a third proportional flow valve in fluid communication with the water supply conduit for controlling the rate of flow of water into the third inlet port of the mixing manifold;

a fluid output conduit fluidly connected to the outlet port of the mixing manifold for receiving a mixture of embalming chemicals and water from the mixing manifold and for delivering said mixture to a cadaver;

a fourth proportional flow valve in fluid communication with the fluid output conduit for controlling the rate of flow of the mixture from the mixing manifold;

a pump fluidly connected to the fluid output conduit and positioned between the mixing manifold and the fourth proportional flow valve; and a controller in electronic communication with the pump, the proportional flow valves and the multi-directional valves, wherein the controller controls the flow and the rate of flow of the embalming chemical from the container to the mixing manifold, the rate of flow of water from the water supply to the mixing manifold, and the rate of flow of the mixture of water and embalming chemical from the mixing manifold, wherein each multi-directional valve selectively allows the flow of an embalming chemical from the plurality of containers into the first conduit or the second conduit to provide a mixture of embalming chemicals entering the mixing manifold for mixing with water.

2. The system of claim 1, wherein the controller is programmed to store at least one predetermined reference value that is equivalent to a desired fluid flow rate, and wherein the controller is further programmed to control each proportional flow valve such that the rate of flow of fluid through said valve is substantially equivalent to the reference value.

3. The system of claim 1, wherein the controller is programmed to store at least one predetermined reference mixture of selected embalming chemicals, and wherein the controller is further programmed to selectively open or close the multi-directional control valves to allow the flow of the selected embalming chemicals into the first and second conduits.

4. The system of claim 1, wherein the controller is a programmable logic controller.

5. The system of claim 4, wherein the controller is manually programmed.

6. The system of claim 4, further comprising a remote control programming device for programming the controller.

7. The system of claim 1, wherein mixing of the fluids and water in the mixing manifold is by cyclonic action.

8. The system of claim 1, further comprising a suction conduit fluidly connected to the fluid output conduit and positioned between the pump and the mixing manifold for aspirating materials from the cadaver, and a multi-directional valve fluidly connected to said conduit.

9. The system of claim 8, further comprising a suction discharge conduit fluidly connected to the fluid output conduit and positioned between the pump and the fourth proportional flow valve for discharging materials aspirated from the cadaver, and a multi-directional valve fluidly connected to said conduit.

10. The system of claim 9, wherein the suction conduit and the suction discharge conduit are in fluid communication with the water supply conduit for flushing of said conduits with water.

11. A continuous flow system for mixing liquids and water, comprising:

a plurality of containers, wherein each container contains a fluid having substantially the same viscosity as water;

a mixing manifold comprising a hollow chamber and having a plurality of inlet ports and an outlet port;

a first fluid supply conduit fluidly connecting a first container of the plurality of containers with a first inlet port of the mixing manifold;

a second fluid supply conduit fluidly connecting a second container of the plurality of containers with a second inlet port of the mixing manifold;

a plurality of other fluid supply conduits, each of the conduits fluidly connecting another container of the plurality of containers with the first and the second fluid supply conduits;

a plurality of multi-directional valves, each valve being fluidly connected to at least one fluid supply conduit, wherein each valve has an open position whereby the fluid flows through the fluid supply conduit and a closed position whereby the fluid cannot flow through the fluid supply conduit;

a first proportional flow valve in fluid communication with the first conduit for controlling the rate of flow of the fluid from the first conduit into the first inlet port of the mixing manifold;

a second proportional flow valve in fluid communication with the second conduit for controlling the rate of flow of the fluid from the second conduit into the second inlet port of the mixing manifold;

a water supply conduit fluidly connected to a water source and to a third inlet port of the mixing manifold;

a third proportional flow valve in fluid communication with the water supply conduit for controlling the rate of flow of water into the third inlet port of the mixing manifold;

a fluid mixture output conduit fluidly connected to the outlet port of the mixing manifold for receiving a mixture of fluids and water from the mixing manifold;

a fourth proportional flow valve in fluid communication with the fluid mixture output conduit for controlling the rate of flow of the fluid mixture from the mixing manifold; and a pump fluidly connected to the fluid output conduit and positioned between the mixing manifold and the fourth proportional flow valve, wherein each multi-directional valve selectively allows the flow of a fluid from the plurality of containers into the first or the second conduits to provide a mixture of fluids entering the mixing manifold.

12. The system of claim 11, further comprising a controller in electronic communication with the pump, the proportional flow valves and the multi-directional valves, wherein the controller controls the flow and the rate of flow of fluid through the conduits.

13. The system of claim 12, wherein the controller is programmed to store at least one predetermined reference value that is equivalent to a desired fluid flow rate, and wherein the controller is further programmed to control each proportional flow valve such that the rate of flow of fluid through each said valve is substantially equivalent to the reference value.

14. The system of claim 13, wherein the controller is programmed to store at least one predetermined reference mixture of selected fluids, and wherein the controller is further programmed to selectively open or close the multi-directional control valves to allow the flow of the selected fluids into the first and second conduits.

15. The system of claim 13, wherein the controller is a programmable logic controller.

16. The system of claim 15, wherein the controller is manually programmed.

17. The system of claim 15, further comprising a remote control programming device for programming the controller.

18. The system of claim 11, wherein mixing of the fluids and water in the mixing manifold is by cyclonic action.

19. An automated method for delivering a mixture of embalming chemicals to a cadaver, comprising the steps of:
   (a) providing a plurality of containers;
   (b) providing an embalming chemical in each of the containers;
   (c) providing a mixing manifold comprising a hollow chamber and having a plurality of inlet ports and an outlet port;
   (d) providing a first embalming chemical supply conduit fluidly connecting a first container of the plurality of containers with a first inlet port of the mixing manifold;
   (e) providing a second embalming chemical supply conduit fluidly connecting a second container of the plurality of containers with a second inlet port of the mixing manifold;
   (f) providing a plurality of other embalming chemical supply conduits, each of the conduits fluidly connecting another container of the plurality of containers with the first and the second fluid supply conduits;
   (g) selectively controlling the flow of embalming chemicals through the plurality of conduits by a plurality of multi-directional valves in electronic communication with a controller;
   (h) selecting an embalming chemical from the plurality of containers;
   (i) continuously flowing a selected embalming chemical through the first conduit and into the first inlet port of the mixing manifold;
   (j) continuously flowing a selected embalming chemical through the second conduit and into the second inlet port of the mixing manifold;
   (k) continuously flowing water from a water supply conduit into a third inlet port of the mixing manifold;
   (l) controlling the rate of flow of embalming chemicals and water into the mixing manifold; and
   (m) continuously delivering a mixture of embalming chemicals and water from the outlet port of the mixing manifold to a cadaver through a fluid output conduit fluidly connected to the outlet port.

20. The method of claim 19, further comprising the step of providing a plurality of proportional flow valves, each of said valves being in fluid communication with one of the first conduit, the second conduit, the water supply conduit or the fluid output conduit, said valves further being in electronic communication with a controller.

21. The method of claim 20, further comprising the steps of programming the controller to store at least one predetermined reference value that is equivalent to a desired fluid flow rate, and further programming the controller to control each proportional flow valve such that the rate of flow of fluid through said valve is substantially equivalent to the reference value.

22. The method of claim 20, further comprising the steps of programming the controller to store at least one predetermined reference mixture of selected embalming chemicals, and further programming the controller to selectively open or close the multi-directional control valves to allow the flow of the selected embalming chemicals into the first and second conduits.

23. An automated method for delivering an embalming chemical to a cadaver, comprising the steps of:
   (a) providing a container containing an embalming chemical;
   (b) providing a manifold comprising a hollow chamber and having an inlet port and having an outlet port fluidly connected to a fluid output conduit;
   (c) providing an embalming chemical supply conduit fluidly connecting the container with the inlet port of the manifold;
   (d) controlling the flow of the embalming chemical through the chemical supply conduit by operating a multi-directional valve in electronic communication with a controller;
   (e) flowing the embalming chemical through the chemical supply conduit and into the inlet port of the manifold;
   (e) controlling the rate of flow of the embalming chemical concentrate into the manifold by operating a proportional control valve in electronic communication with the controller; and
   (f) flowing the embalming chemical through the fluid output conduit to the cadaver.

24. The method of claim 23, further comprising the steps of programming the controller to store at least one predetermined reference value that is equivalent to a desired fluid flow rate, and further programming the controller to control the proportional valve such that the rate of flow of fluid through said valve is substantially equivalent to the reference value.

* * * * *